United States Patent [19]

Gander

[11] 4,310,546
[45] Jan. 12, 1982

[54] NOVEL RETINOIDS AND THEIR USE IN PREVENTING CARCINOGENESIS

[75] Inventor: Robert J. Gander, Whitehouse, N.J.

[73] Assignee: Johnson & Johnson, New Brunswick, N.J.

[21] Appl. No.: 929,093

[22] Filed: Jul. 31, 1978

[51] Int. Cl.³ .................... A61K 31/22; A61K 31/23; C11C 3/00
[52] U.S. Cl. .................................. 424/311; 260/404; 424/312

[58] Field of Search .............................. 260/404, 410.9; 424/311, 312

[56] References Cited

U.S. PATENT DOCUMENTS 4,108,880  8/1978  Gander et al. .................. 260/410.5

Primary Examiner—Jerome D. Goldberg
Attorney, Agent, or Firm—Irving Newman

[57] ABSTRACT

Novel N-(4-acyloxyphenyl)-all-trans-retinamide compounds are useful in preventing epithelial cancer in mammals.

17 Claims, No Drawings

NOVEL RETINOIDS AND THEIR USE IN PREVENTING CARCINOGENESIS

TECHNICAL FIELD

This invention relates to certain novel retinoids, more particularly, certain N-(4-acyloxyphenyl)-all-trans-retinamides, and to their use to prevent the development of various forms of epithelial cancer in mammals.

BACKGROUND ART

As pointed out in a paper entitled "Approaches to Prevention of Epithelial Cancer During The Preneoplastic Period", *Cancer Research*, 36 (July, 1976), 2699–2702, presented at a Conference on "Early Lesions and The Development of Epithelial Cancer" (National Cancer Institute, Oct. 21–23, 1975), the death rates for several common forms of epithelial cancer either increased or showed no decrease during the 20-year period from 1950 to 1970. These epithelial cancer sites included the lung and pancreas in both men and women, the colon and bladder in men, the breast and ovary in women. The conventional clinical approach that has been followed with most epithelial cancer has been to wait until the patient has invasive disease and then treat this disease with cytotoxic chemotherapy, surgery, or radiation. None of these modalities has been overwhelmingly successful for the treatment of all types of epithelial cancer, in spite of some advances that have occurred.

Accordingly, it has been suggested that an alternative approach to the problem of epithelial cancer is to consider the disease as a process which takes many years to reach its final, invasive stage in man and which might be controlled by physiological or pharmacological mechanisms during its early stages, with the goal of prevention of end-stage, invasive, terminal disease.

Retinoids play an essential role in controlling the normal differentiation of epithelial tissues and are therefore important for controlling premalignant epithelial cell differentiation. It has even been found that retinoids can cause cellular repair of hyperplastic and anaplastic lesions caused by chemical carcinogens. Moreover, retinoid deficiency has been shown, in experimental animals, to enhance susceptibility to chemical carcinogenesis. Indeed, retinoids are essential for the normal cellular differentiation of epithelia that account for more than half of the total primary cancer in both men and women. These epithelia include those of the bronchi and trachea, stomach, intestine, uterus, kidney and bladder, testis, prostate, pancreatic ducts, and skin. In the absence of retinoids in the diet, normal cellular differentiation does not occur in these epithelia.

However, natural retinyl esters, such as retinyl acetate and retinyl palmitate, as well as retinoic acid, have been found to be too toxic at high dosage levels to be of practical value for cancer prevention in higher mammals. Progress has been made recently in identifying synthetic retinoids, for example 13-cis-retinoic acid, that are considerably less toxic than retinoic acid or the natural retinyl esters, and are also more potent in preventing chemical carcinogenesis. See "13-cis-Retinoic Acid:Inhibitor of Bladder Carcinogenesis in the Rat", *Science*, Feb. 4, 1977, Volume 195, pp 487–489 as well as "13-cis-Retinoic Acid: Inhibition of Bladder Carcinogenesis Induced in Rats by N-Butyl-N-(4-hydroxybutyl) nitrosamine", *Science*, Nov. 18, 1977, Volume 198, pages 743–744. 13-cis-retinoic acid, however, has not been found to be particularly effective against breast cancer in the rat model discussed hereinafter.

Recent developments in this field, as summarized above, are also discussed in an article entitled "Prevention of Chemical Carcinogenesis by Vitamin A and its Synthetic Analogs (Retinoids)", *Federation Proceedings*, 35, (May 1, 1976), 1332–1338, in which it is noted that it still remains a goal to find, for practical application to man and other mammals, highly effective synthetic retinoids that also have low toxicity and a high degree of tissue specificity against cancer at any particular organ site. See also the articles in the Fall, 1977, issue of *The Southern Research Institute Bulletin* (Volume 30, Number 2), pages 3–9 ("CHEMOPREVENTION OF CANCER—Steps Leading to Some Malignancies May Be Reversible" and "How Do Retinoids Work? Studies on Retinoic Acid-Binding Protein"). Other recent publications of interest in this field include "Biological Activity and Metabolism of the Retinoid Axerophthene (Vitamin A Hydrocarbon)", *Cancer Research* 38, 1734–1738, June 1978; and "Retinoids and Cancer Prevention: The importance of the Terminal Group of the Retinoid Molecule In Modifying Activity and Toxicity" in *Carcinogens: Identification and Mechanism of Action*, A. C. Griffin & C. R. Shaw, Editors, N.Y. Raven Press, 1978 (in Press).

DISCLOSURE OF INVENTION

Certain novel N-(4-acyloxyphenyl)-all-transretinamides, more particularly those compounds having the structure:

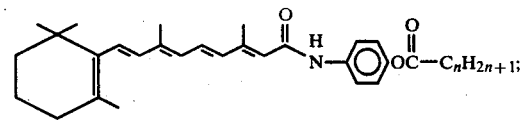

wherein n is 1–18, have the desirable combination of properties of (1) low systemic toxicity, (2) good effectiveness in preventing epithelial cancer in mammals at reasonable dose levels, and (3) adequate target specificity in concentrating at one or more common sites of epithelial cancer in mammals, such as the breast, bladder, colon, lungs and pancreas.

BEST MODE FOR CARRYING OUT THE INVENTION

In use for the prevention of carcinogenesis, the N-(4-acyloxphenyl)-all-trans-retinamide compounds of the present invention are administered systemically, preferably orally, in a pharmaceutically acceptable vehicle compatible therewith at a dosage level effective to prevent or retard carcinogenesis but below that which would be toxic. The drug is administered at regular intervals, conveniently at meal times or once daily. Doses of the order of 50 mg/kg/day or less are effective in preventing epithelial cancer.

EXAMPLE 1

N-(4-Acetoxyphenyl)-all-trans-Retinamide

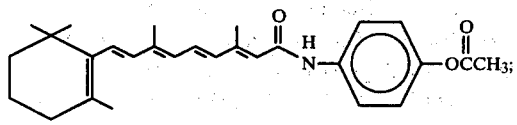

In a foil-covered three-neck flask was placed a solution of 5.00 g. (0.0129 mole) of N-(4-hydroxyphenyl)-all-trans-retinamide in 10 ml. of pyridine. (The preparation of N-(4-hydroxyphenyl)-all-trans-retinamide is described in prior United States Patent Application Ser. No. 628,177, filed Nov. 3, 1975, now U.S. Pat. No. 4,108,880.) To this was added a solution of 1.65 g. (0.0162 mole) of acetic anhydride in 5 ml. of pyridine. The flask was then immersed in an oil bath at 95° C. for one hour, during which the contents were swept with nitrogen and stirred with a magnetic stirrer. The reaction mix was then cooled to room temperature in ice and poured into 150 ml. of cold distilled water. The yellow solid which separated and the aqueous phase were transferred to a separatory funnel and shaken with 300 ml. of ethyl ether until the solid dissolved. The aqueous phase was discarded, and the ether phase was washed with four 50-ml. portions of cold distilled water. The ether was dried over sodium sulfate, filtered, and evaporated in vacuo. The yellow solid residue was recrystallized from methanol (40. ml. per gram). The product melted at 179°–181° C. Its proton magnetic resonance spectrum was consistent with the structure with no extraneous resonances.

Anal. Calcd. for $C_{28}H_{35}NO_3$: C, 77.6 H, 8.14 N, 3.23. Found: C, 77.3 H, 8.05 N, 3.09.

EXAMPLE 2

N-(4-Propionyloxyphenyl)-all-trans-Retinamide

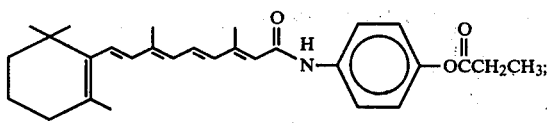

In a foil-covered three-neck flask was placed a solution of 5.00 g. (0.0128 mole) of N-(4-hydroxyphenyl)-all-trans-retinamide in 10 ml. of pyridine. To this was added a solution of 2.08 g. (0.0160 mole) of propionic anhydride in 5 ml. of pyridine. The flask was then immersed in an oil bath at 95° C. for one hour, during which the contents were swept with nitrogen and stirred with a magnetic stirrer. The reaction mix was then cooled to room temperature in ice and poured into 150 ml. of cold, distilled water. The yellow solid which separated and the aqueous phase were transferred to a separatory funnel and shaken with 200 ml. of ethyl ether until the solid dissolved. The aqueous phase was discarded, and the ether phase was washed with four 40-ml. portions of cold distilled water. The ether was dried over sodium sulfate, filtered, and evaporated in vacuo. The yellow solid residue was recrystallized from methanol (34 ml. per gram). The product melted at 170°–171° C. Its proton magnetic resonance spectrum was consistent with the structure with no extraneous resonances.

Anal. Calcd. for $C_{29}H_{37}NO_3$: C, 77.8 H, 8.33 N, 3.13. Found: C, 77.7 H, 8.16 N, 3.01.

EXAMPLE 3

N-(4-n-Butyryloxyphenyl)-all-trans-Retinamide

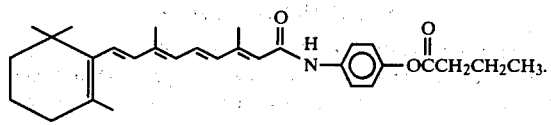

In a foil-covered three-neck flask was placed a solution of 5.00 g. (0.0128 mole) of N-(4-hydroxyphenyl)-all-trans-retinamide in 10 ml. of pyridine. To this was added a solution of 2.53 g. (0.0160 mole) of n-butyric anhydride in 5 ml. of pyridine. The flask was then immersed in an oil bath at 95° C. for one hour, during which the contents were swept with nitrogen and stirred with a magnetic stirrer. The reaction mix was then cooled to room temperature in ice and poured into 150 ml. of cold, distilled water. The precipitate which separated was filtered, washed with water and dried in vacuo. The dry solid was recrystallized from 1:1 chloroform-hexane (10 ml. per gram). Its proton magnetic resonance spectrum was consistent with the structure with no extraneous resonances. It melted at 175°–176° C.

Anal. Calcd. for $C_{30}H_{39}NO_3$: C, 78.0 H, 8.52 N, 3.03. Found: C, 78.0 H, 8.45 N, 3.03.

EXAMPLE 4

N-(4-acetoxyphenyl)-all-trans-retinamide and N-(4-propionyloxyphenyl)-all-trans-retinamide were compared with retinoic acid in an in vitro screening model for identifying retinoids having activity in preventing carcinogenesis in epithelial tissue. The experimental method, which is described in *Experimental Lung Cancer: Intern'l Symp*, 575–82, 1974, involves reversal of keratinization in tracheal organ culture.

In brief summary, in the absence of retinoic acid or a synthetic retinoid having similar activity, the test organ culture of tracheal epithelium undergoes abnormal differentiation. Addition of small concentrations of retinoic acid (as low as $10^{-9}$ M) will cause reversion of normal tracheal epithelium. Test compounds are compared in activity to retinoic acid or another active standard both as regards squamous metaplasia and keratin production, both of which are measures of abnormal development of the epithelial culture.

In the tests reported in Table I below, all tracheas were cultured for the first 3 days in medium without retinoid. At this time, some tracheas were collected, while the rest were cultured for a further week in medium containing either no retinoid, or retinoid added at the concentrations shown. These tracheas were collected on the 10th day of culture. Cultures were graded as to the percentage of their total epithelium showing squamous metaplasia on eight cross sections from the middle of each trachea. If more than 40% of the total epithelial length was squamous, it was graded as having severe squamous metaplasia; between 10–40% was graded as marked; between 2–10% was graded as mild; and less than 2% was graded as minimal.

The results, summarized in Table I below, show that both the 4-acetoxyphenyl retinamide and the 4-propionyloxyphenyl retinamide exhibit the same order of magnitude of activity as retinoic acid at a concentration of $10^{-8}$ M. At $10^{-9}$ M the propionyloxphenyl retinamide is again substantially as active as retinoic acid, while the acetoxyphenyl retinamide is somewhat less active in reversing keratinization.

TABLE I

Reversal of Keratinized Squamous Metaplastic Lesions of Vitamin A Deficiency in Tracheal Organ Cultures Treated with Retinoids

| Treatment of Cultures (number of cultures) | | % of Cultures with Respective Amounts of Squamous Metaplasia | | | | | % of Cultures with Keratin and Keratohyaline Granules |
|---|---|---|---|---|---|---|---|
| | | None | Minimal | Mild | Marked | Severe | |
| No Retinoid, collected day 3 | (152) | 12 | 8 | 42 | 26 | 79 | 71 |
| No Retinoid collected day 10 | (140) | 1 | 2 | 11 | 50 | 34 | 95 |
| Retinoic Acid | | | | | | | |
| $10^{-8}$ M | (26) | 27 | 49 | 23 | 0 | 0 | 0 |
| $10^{-9}$ M | (134) | 16 | 37 | 32 | 12 | 2 | 3 |
| $10^{-10}$ M | (47) | 9 | 4 | 43 | 17 | 28 | 32 |
| 4-Acetoxyphenyl Retinamide | | | | | | | |
| $10^{-8}$ M | (5) | 40 | 60 | 0 | 0 | 0 | 0 |
| $10^{-9}$ M | (6) | 0 | 17 | 33 | 50 | 0 | 33 |
| 4-Propionyloxyphenyl Retinamide | | | | | | | |
| $10^{-8}$ M | (5) | 20 | 40 | 20 | 20 | 0 | 0 |
| $10^{-9}$ M | (5) | 0 | 40 | 40 | 20 | 0 | 0 |

EXAMPLE 5

N-(4-propionyloxyphenyl)-all-trans-retinamide was compared to retinyl acetate in the experimental assay for efficacy against rat breast cancer described in *Nature*, Vol. 267, pp 620-621 (June 16, 1977), which measures the ability to inhibit mammary carcinogenesis induced by N-methyl-N-nitrosourea (MNU). The test conditions and results after 8 weeks of testing are set forth in Table II. Not only is the 4-propionyloxyphenyl retinamide substantially as efficacious as retinyl acetate, it is also less toxic, as shown by the mean weight data.

TABLE II

Effect of 4-Propionyloxyphenyl Retinamide On N-Methyl-N-Nitrosourea (MNU)-Induced Mammary Cancer (8 Weeks)

| Carcinogen | Retinoid | Mammary Tumor Incidence, 4-20-78 | | Total No. of Tumors | Mean Weight |
|---|---|---|---|---|---|
| Saline | Placebo | 0/6 | (0%) | 0 | 249 |
| Saline | Retinyl Acetate | 0/6 | (0%) | 0 | 223 |
| Saline | 4-Acetoxyphenyl Retinamide | 0/6 | (0%) | 0 | 243 |
| Saline | 4-Propionyloxyphenyl Retinamide | 0/6 | (0%) | 0 | 237 |
| MNU, high dose | Placebo | 14/24 | (58%) | 24 | 237 |
| MNU, high dose | 4-Retinyl Acetate | 6/12 | (50%) | 11 | 224 |
| MNU, high dose | 4-Acetoxyphenyl Retinamide | 6/12 | (50%) | 11 | 238 |
| MNU, high dose | 4-Propionyloxyphenyl Retinamide | 3/12 | (25%) | 4 | 235 |

Animals: Female Sprague-Dawley rats obtained from ARS Sprague-Dawley.
Carcinogen: Crystalline MNU. Rats received 2 I.V. injections at 50 and 57 days of age. High dose is 50 mg/kg.
Retinoids: Retinoids were dissolved in solvent and blended into the diets. Rats were placed on diets 3 days after last MNU injection. All doses were 1 millimole/kg diet.
Retinoid Solvent: 50 gm trioctanoin:ethanol (3:1), 0.05 ml Tenox 20, 0.05 ml DL-α-Tocopherol/kg Wayne lab meal.
Retinoid Placebo: 50 gm retinoid solvent/kg/diet.

Variations can, of course, be made without departing from the spirit and scope of the invention.

What is claimed is:

1. An N-(4-acyloxyphenyl)-all-trans-retinamide having the structure:

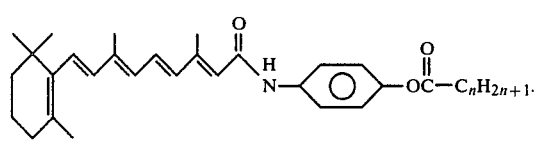

wherein n is an integer from 1 through 18.

2. An N-(4-acyloxyphenyl)-all-trans retinamide according to claim 1 selected from the group consisting of N-(4-acetoxyphenyl)-all-trans-retinamide, N-(4-propionyloxyphenyl)-all-trans-retinamide and N-(4-butyryloxyphenyl)-all-trans-retinamide.

3. N-(4-acetoxyphenyl)-all-trans-retinamide according to claim 1.

4. N-(4-propionyloxyphenyl)-all-trans-retinamide according to claim 1.

5. N-(4-butyryloxyphenyl)-all-trans-retinamide according to claim 1.

6. A composition for the treating carcinogenesis in epithelial tissue comprising an effective amount for treating carcinogenesis of a retinamide of claim 1 in a pharmaceutically acceptable vehicle compatible therewith.

7. The composition of claim 6 in which said retinamide is N-(4-acetoxyphenyl)-all-trans-retinamide.

8. The composition of claim 6 in which said retinamide is N-(4-propionyloxyphenyl)-all-trans-retinamide.

9. The composition of claim 6 in which said retinamide is N-(4-butyryloxyphenyl)-all-trans-retinamide.

10. The composition of claim 6 in oral dosage form.

11. A method of treating carcinogenesis in epithelial tissue in a mammal in need of said treatment, which comprises periodically administering to the subject mammal an effective amount for treating carcinogenesis of a retinamide of claim 1.

12. The method of claim 11 wherein said retinamide is administered orally.

13. The method of claim 12 wherein said retinamide is administered at least once daily.

14. The method of claim 11 wherein said retinamide is administered in an amount up to about 50 mg/kg/day.

15. The method of claim 11 wherein said retinamide is N-(4-acetoxyphenyl)-all-trans-retinamide.

16. The method of claim 11 wherein said retinamide is N-(4-propionyloxyphenyl)-all-trans-retinamide.

17. The method of claim 11 wherein said retinamide is N-(4-butyryloxyphenyl)-all-trans-retinamide.

* * * * *